US009700496B2

(12) United States Patent
Kurfurst et al.

(10) Patent No.: US 9,700,496 B2
(45) Date of Patent: Jul. 11, 2017

(54) COSMETIC COMPOSITION CONTAINING A PARTICULAR WATER, AND USE THEREOF AS A DEPIGMENTING OR ANTI-AGEING AGENT

(71) Applicant: LVMH RECHERCHE, Saint Jean de Braye (FR)

(72) Inventors: Robin Kurfurst, Saint Jean de Braye (FR); Kristell Lazou, Orleans (FR); Eric Perrier, Les Cotes d'Arey (FR)

(73) Assignee: LVMH RECHERCHE, Saint Jean de Braye (FR)

( * ) Notice: Subject to any disclaimer, the term of this patent is extended or adjusted under 35 U.S.C. 154(b) by 0 days.

(21) Appl. No.: 14/075,807

(22) Filed: Nov. 8, 2013

(65) Prior Publication Data
US 2014/0072522 A1 Mar. 13, 2014

Related U.S. Application Data

(62) Division of application No. 13/187,221, filed on Jul. 20, 2011, now abandoned.

(30) Foreign Application Priority Data

Jul. 21, 2010 (FR) ...................................... 10 55942
Jun. 17, 2011 (FR) ...................................... 11 55359

(51) Int. Cl.
| | |
|---|---|
| *A61K 8/19* | (2006.01) |
| *A61Q 19/02* | (2006.01) |
| *A61Q 19/08* | (2006.01) |
| *A61K 8/20* | (2006.01) |
| *A61K 8/23* | (2006.01) |
| *A61K 8/96* | (2006.01) |

(52) U.S. Cl.
CPC .................. *A61K 8/19* (2013.01); *A61K 8/20* (2013.01); *A61K 8/23* (2013.01); *A61K 8/965* (2013.01); *A61Q 19/02* (2013.01); *A61Q 19/08* (2013.01); *A61K 2800/782* (2013.01)

(58) Field of Classification Search
None
See application file for complete search history.

(56) References Cited

U.S. PATENT DOCUMENTS

| | | | |
|---|---|---|---|
| 5,928,631 A * | 7/1999 | Lucas ....................... | A61K 8/19 422/5 |
| 2003/0072724 A1 | 4/2003 | Maibach et al. | |
| 2005/0180938 A1 | 8/2005 | Novelli | |
| 2008/0081085 A1* | 4/2008 | Mitra ........................ | A61K 8/97 424/777 |

FOREIGN PATENT DOCUMENTS

| | | |
|---|---|---|
| EP | 1166764 | 1/2002 |
| FR | 2909383 | 6/2008 |
| JP | 2009-013075 | 1/2009 |
| JP | 2011-026318 | 2/2011 |
| WO | WO 2005/032507 | 4/2005 |
| WO | WO 2009/091183 | 7/2009 |
| WO | WO 2009091183 A2 * | 7/2009 |

OTHER PUBLICATIONS

Icelandic Glacial (Icelandic Glacial: "Spring Water—Still", Internet Citation, Jan. 2003, p. 1-2; on Nov. 8, 2013 IDS).*
Iceland Spring (http://web.archive.org/web/20090520083021/http://icelandspring.com/certifications.html, "Iceland Spring Bottled Water Certification", Internet Archive, May 20, 2009; on Nov. 8, 2013 IDS).*
Maletis (http://web.archive.org/web/20071219022043/http://www.maletis.com/product-category-sub.php?category=9, "Water Products", Internet Archive, Dec. 19, 2007; on Nov. 8, 2013 IDS).*
Skyn Iceland, "Solutions for Stressed Skin", website accessed via Internet Archive Wayback Machine, Mar. 29, 2010.*
Database CAPLUS, Chemical Abstracts Service, 2009, "Skin-lightening marine minerals", XP002627997, Database accession No. 2009:348011—1 page.
Icelandic Glacial: "Spring Water—Still", Internet Citation, Jan. 2003, pp. 1-2, XP007917526.
NSF International: "Test Report USFDA 50 State—Source—(AB) (Icelandic Glacial—Source) Icelandic Water Holdings EHF", Internet Citation, Mar. 2010, 11 pages, XP007917373.
"Icelandic Mineral Waters Firming Gel Moisturizer", Avon, Jul. 2006, XP002672126.
Mintel, "Icelandic Relief Eye Cream", Skyn Iceland, Sep. 2006, XP002672127.
Mintel, "Anti-Blemish Gel", Skyn Iceland, Sep. 2006, XP002672128.
Mintel, "The Antidote SPF 18 Mineral Sunscreen", Skyn Iceland, Jul. 2007, XP002672129.
"Dior Announces Collaboration with Icelandic Glacial", Dec. 7, 2010, XP002672130.

(Continued)

*Primary Examiner* — Ali Soroush
*Assistant Examiner* — Genevieve S Alley
(74) *Attorney, Agent, or Firm* — Hamre, Schumann, Mueller & Larson P.C.

(57) ABSTRACT

The invention relates to the use, in a cosmetic or dermatological composition, of a particular water having a pH of between 7.8 and 10 and a total dissolved solids (TDS) concentration of between 10 and 250 mg/l. The invention also relates to a cosmetic or dermatological composition containing this water.

The invention relates in particular to a treatment method intended for preventing or delaying the appearance of the effects of intrinsic and/or extrinsic ageing of the skin, or for slowing down the effects thereof; for preventing or reducing pigmentary spots on the skin, or the coloration of hyperpigmented areas of skin; for reducing the pigmentation of the periphery of depigmented areas; for improving the uniformity of the skin coloration; or for lightening the complexion of the skin.

21 Claims, 4 Drawing Sheets

(56) References Cited

OTHER PUBLICATIONS

Miura Co., "Soft water is like hot spring water", Apr. 23, 2008, XP002672131.
http://web.archive.org/web/20090219081106/http://www.thebeautyinsiders.com/skyn-iceland-arctic-brightening-serum.htm; "Skyn Iceland Arctic Brightening Serum Overview", wayback machine date Feb. 19, 2009.
http://www.cosmeticbusiness.com/news/article_page/Dior_to_use_only_Icelandic_Glacial_spring_water/58301; "Dior to use only Icelandic Glacial spring water" Dec. 15, 2010.
Barolet et al.: "Beneficial effects of spraying low mineral content thermal spring water after fractional photothermolysis in patients with dermal melasma", Journal of Cosmetic Dermatology, vol. 8 , No. 2, 2009 pp. 114-118.
Iceland Spring (http://web.archive.org/web/20090520083021/http://icelandspring.com/certifications.html, "Iceland Spring Bottled Water Certification", Internet Archive, May 20, 2009.
Maletis (http://web.archive.org/web/20071219022043/http://www.maletis.com/product-category-sub.php?category=9, "Water Products", Internet Archive, Dec. 19, 2007.

\* cited by examiner

COSMETIC COMPOSITION CONTAINING A PARTICULAR WATER, AND USE THEREOF AS A DEPIGMENTING OR ANTI-AGEING AGENT

The subject of the present invention is a cosmetic or dermatological composition containing a particular water, the use of this water as a cosmetic agent, and also a cosmetic or dermatological method of treatment comprising the topical application, to the skin or keratin fibres, of this water or of a composition containing same.

The invention also relates to the use of this particular water as a cosmetic agent for depigmenting, lightening or bleaching the skin or keratin fibres, and also to the use of this water as a cosmetic anti-ageing agent.

PRIOR ART

Intrinsic ageing of the skin, the external attacks to which it is subjected, such as exposure to ultraviolet radiation from the sun, or hormonal variations, induce detrimental modifications therein. These events modify the histology of the skin, its visible quality and its beauty, and induce the appearance of characteristic clinical signs such as wrinkles, inflammatory reactions, a loss of elasticity, reduced moisturisation or else a heterogeneous pigmentation which manifests itself in the appearance of brown spots, for instance lentigines, in particular on the back of the hands, or on the face, the neckline or else the top of the head.

Dry skin is known to be skin that is not very luminous, has no radiance and is subject to pigmentary disorders. External attacks such as UV radiation, wind, temperature variations and pollution cause or reinforce dryness of the skin by making the skin barrier fragile.

The present invention focuses on intrinsic ageing or on extrinsic ageing of the skin, and also on skin pigmentation conditions, which may or may not be linked to ageing of the skin.

Extrinsic ageing of the skin is induced by excessive chemical and physical stimulations—such as exposure to the sun, exposure to light, exposure to UV radiation, stress and pollution—which damage the normal functions of the skin and cause the appearance of clinical signs of detrimental modifications, such as wrinkles and a loss of firmness, of suppleness and of elasticity, essentially caused by detrimental cell and tissue modifications in the epidermis, for instance the disruption of keratinocyte differentiation, or collagen fibre degradation in the dermis which results from the enzymatic activity of metalloproteinases (MMPs), in particular metalloproteinase-1 (MMP-1).

Concomitantly, intrinsic or chronological ageing is the consequence of genetically programmed ageing in which endogenous factors are involved. This intrinsic ageing is caused by cell metabolism dysfunctions resulting in the accumulation of damage on DNA and dysregulation of biochemical pathways—such as the regulation of degradation enzymes, the resistance to oxidative stress or else the loss of the ability to synthesize a functional extracellular matrix—which are reflected, for example, by histological changes such as the appearance of wrinkles and/or fine lines and the modification of elastic fibres.

In humans, pigmentation results from the synthesis and distribution of melanin pigments in keratin materials such as the skin, the follicles or the hair. It is regulated by many internal or external factors.

Skin and keratin fibre pigmentation results from the metabolic activity of specialized cells, the melanocytes. These dendritic cells of the epidermis originate from undifferentiated precursors of the neural crest during embryogenesis, the melanoblasts. The melanocytes produce melanin in organelles called melanosomes, which are transferred to the neighbouring keratinocytes via their dendrites.

The overproduction of melanin causes heterogeneities in skin coloration, for example lentigines.

Many anti-ageing and/or depigmenting techniques and substances are known which aim, for aesthetic or cosmetic purposes,
  i) to prevent or delay the appearance of the signs of extrinsic and/or intrinsic ageing of the skin, or ii) to slow down or reduce the effects thereof, and/or
  i) to improve the uniformity of the skin colour, ii) to lighten the skin complexion, or iii) to correct or reduce pigmentary spots on the skin.

The search for new anti-ageing and/or depigmenting substances which are effective and devoid of toxicity is therefore a necessity in the cosmetic industry.

PURPOSES OF THE INVENTION

The main purpose of the invention is to solve the technical problem consisting of the provision of a novel cosmetic agent and of a cosmetic composition containing same, said agent and said composition being intended for preventing or delaying the appearance of the signs of extrinsic and/or intrinsic ageing of the skin, or for slowing down or reducing the effects thereof.

The purpose of the invention is also to provide a cosmetic or dermatological care method, and in particular a cosmetic skin care method, i) for preventing or delaying the appearance of the signs of extrinsic and/or intrinsic ageing of the skin, or ii) for slowing down or reducing the effects thereof, at least in areas exhibiting such signs.

The purpose of the invention is also to solve the technical problem consisting of the provision of a cosmetic composition having properties of bleaching, lightening or depigmenting the skin or keratin fibres. The purpose of the invention is also to provide a cosmetic or dermatological care method, and in particular a method of skin and keratin fibre care by carrying out bleaching, lightening or depigmentation of the skin or keratin fibres, at least in hyperpigmented areas.

The purpose of the invention is also to find a novel inexpensive cosmetic active agent which is available in sufficient amount for the cosmetic or dermatological industry, and the use of which is readily industrializable.

SUMMARY OF THE INVENTION

Thus, a subject of the present invention is the use of a particular water as a cosmetic agent, a cosmetic composition containing this water which has properties of prevention and repair of extrinsic and/or intrinsic skin ageing, and also a cosmetic or dermatological care method comprising the topical application of this water or of this composition to keratin materials.

A subject of the present invention is also a cosmetic or dermatological composition which has properties of bleaching, lightening or depigmenting the skin and/or keratin fibres.

The inventors of the present invention have discovered, very surprisingly, that this particular water, referred to as "water of the invention" in the description which follows, has:

on normal human keratinocytes (NHKs), a modulatory activity on the expression of the gene encoding HSP-70 (Heat Shock Protein 70 KDa or HSPA1A/HSPA1B) and/or of the gene encoding involucrin, and on normal human fibroblasts (NHFs), a modulatory activity on the expression of the gene encoding MMP-1 and/or of the gene encoding MMP-3.

They have demonstrated that the water used according to the invention induces an increase in the expression of the product of the genes encoding HSP-70 and involucrin, and causes an inhibition of the expression of the genes encoding MMP-1 and MMP-3. The increase in expression of the gene encoding HSP-70 confers, on the keratinocytes, better resistance to stresses and to external attacks, which can be reflected, for example, by a reduction in apoptosis. Under these conditions, the keratinocytes secrete less cytokines and chemokines, which are pro-inflammatory factors involved in extracellular matrix degradation and in the stimulation of melanogenesis. Likewise, the stimulation of the expression product of the gene encoding involucrin, which is a key factor in keratinocyte differentiation, allows the formation of an epidermal barrier which is protective with respect to external attacks. The reduction in the product of the genes encoding metalloproteinases 1 and 3, which are extracellular matrix degradation enzymes, that are activated, for example, in response to a UV exposure or an oxidative stress, results in a decrease in the expression of these enzymes and, consequently, in a reduction in extracellular matrix degradation via the degradation of collagen, for example.

All these actions maintain skin homeostasis and the proliferation/differentiation equilibrium of the epidermis, which are key factors for an activity of skin protection, and of prevention with respect to pigmentary disorders and extrinsic and/or intrinsic ageing of the skin.

They have also discovered, very surprisingly, that the water of the invention has, on normal human melanocytes (NHMs), a modulatory activity on the expression of the gene encoding tyrosinase-related-protein-1 (TRP-1) and/or of the gene encoding tyrosinase, which are key enzymes in melanogenesis.

They have demonstrated that the water used according to the invention has an inhibitory effect on the expression of the TRP-1 and tyrosinase genes. Such an inhibitory effect on the expression of genes encoding proteins involved in melanogenesis makes it possible to carry out an inhibition of melanogenesis inducing an activity of bleaching, lightening or depigmenting the skin and/or keratin fibres.

DETAILED DESCRIPTION OF THE INVENTION

According to a first subject, the present invention relates to a cosmetic or dermatological composition comprising a water and to the use, in a cosmetic or dermatological composition, of a water, the water having:

a pH of between 7.6 and 10, and preferably between 7.8 and 8.8, more preferably between 7.8 and 8.6, and a total dissolved solids (TDS) concentration of between 10 and 250 mg/l, and preferably between 20 and 100 mg/l.

The concentration by weight of water relative to the total weight of the composition is preferably from 10% to 99%, more preferably from 15% to 95%, and most preferably from 30% to 85%.

The concentration by weight of water relative to the total weight of the composition is for example from 10% to 99%, from 15% to 95%, from 40% to 85% or from at 60% to 80%.

It is possible to define a water according to various parameters resulting from a physicochemical analysis, and in particular according to:

its total dissolved solids (TDS) concentration, expressed in mg/l, with the following classification:

TABLE 1

| | |
|---|---|
| Super low | 0-50 mg/l |
| Low | 50-250 mg/l |
| Medium | 250-800 mg/l |
| High | 800-1500 mg/l |
| Very high | >1500 mg/l | its pH, with the following classification:

TABLE 2

| | |
|---|---|
| Acidic | pH 5-6.7 |
| Neutral | pH 6.7-7.3 |
| Slightly alkaline | pH 7.3-7.8 |
| Alkaline | pH 7.8-10 |

Advantageously, the water of the invention comprises the following concentrations:

calcium ($Ca^{2+}$) between 3 and 14 mg/l, and preferably between 4 and 10 mg/l;

chloride ($Cl^-$) between 2 and 16 mg/l, and preferably between 8 and 14 mg/l;

magnesium ($Mg^{2+}$) between 0.8 and 5 mg/l, and preferably between 0.8 and 3 mg/l;

potassium ($K^+$) between 0.01 and 2 mg/l, and preferably between 0.1 and 1 mg/l;

sodium ($Na^+$) between 2 and 14 mg/l, and preferably between 8 and 13 mg/l;

bicarbonates ($HCO_3^-$) between 0 and 50 mg/l, and preferably between 10 and 40 mg/l;

sulphates ($SO_4^{2-}$) between 1 and 8 mg/l, and preferably between 2 and 5 mg/l.

Preferably, the water of the invention has a pH of between 7.9 and 8.4, or a pH of between 8.2 and 8.8.

The water of the invention advantageously has a total dissolved solids (TDS) concentration of between 50 and 100 mg/l, and preferably between 40 and 80 mg/l, more preferably between 55 and 75 mg/l.

Advantageously, the water of the invention is water originating from a particular spring.

The expression "water from a spring" is intended to mean a water derived from underground water, advantageously naturally suitable for human consumption. This water can be removed from deep down, for example by boring, or else at the surface, for example in the case of a resurgence.

According to a first preferred variant, the water of the invention is extracted from the Hlidarendi (also spelt "Hlíð arendi") spring in the Ölfus region, in Iceland. This spring is supplied by rainwater runoff and melting snow and ice, over volcanic ground.

This water is sold under the name Icelandic Glacial® by the company Icelandic Water Holdings ehf, and distributed, for example, in France by International Breweries & Beers (IBB), Raimbeaucourt 59283—France.

This water can in particular be characterized by the following composition:

calcium ($Ca^{2+}$) approximately 6.4 mg/l;

chlorine ($Cl^-$) approximately 13 mg/l;

magnesium ($Mg^{2+}$) approximately 2.4 mg/l;

potassium ($K^+$) approximately 0.6 mg/l;

sodium ($Na^+$) approximately 12 mg/l;

bicarbonates ($HCO_3^-$) approximately 33 mg/l;
sulphates ($SO_4^{2-}$) approximately 3.4 mg/l;
TDS approximately 62 mg/l;
and has a pH of approximately 8.4.

According to a second preferred variant, the water of the invention is extracted from a spring located at Heiðmörk, in Iceland.

This water is sold under the name Iceland Spring® by the company Icelandic Spring Inc., USA.

This water can in particular be characterized by the following composition:
calcium ($Ca^{2+}$) approximately 4.6 mg/l;
chlorine ($Cl^-$) approximately 11.0 mg/l;
magnesium ($Mg^{2+}$) approximately 0.9 mg/l;
potassium ($K^+$) approximately 0.5 mg/l;
sodium ($Na^+$) approximately 12 mg/l;
sulphates ($50_4^{2-}$) approximately 2.3 mg/l;
TDS approximately 48 mg/l;
and has a pH of approximately 8.7.

According to a third variant, the water of the invention is extracted from a spring located at Monte Zuccone in the Parma Appenines, Emilia-Romagna, Italy.

This water is sold under the name Ducale® by the company Norda.

This water can in particular be characterized by the following composition:
calcium ($Ca^{2+}$) approximately 12.5 mg/l;
chlorine ($Cl^-$) approximately 3.8 mg/l;
magnesium ($Mg^{2+}$) approximately 1.3 mg/l;
potassium ($K^+$) approximately 0.4 mg/l;
sodium ($Na^+$) approximately 3 mg/l;
sulphates ($50_4^{2-}$) approximately 6.9 mg/l;
TDS approximately 56 mg/l;
and has a pH of approximately 8.3.

The values given here are average values, the composition of the water being stable over time. Variations relative to this average value, in particular linked to the method of analysis, can however be observed.

The composition is analysed according to method 200.7 of the US-EPA (United States Environmental Protection Agency) for the calcium, potassium, magnesium and sodium ions; US-EPA 300.0 for the chloride, nitrate, bicarbonate and sulphate ions; SM 2540-C for the total dissolved solids (TDS) concentration; and SM 4500-HB for the pH.

According to one particular variant, the water of the invention is used as a cosmetic agent for the protection and the prevention of extrinsic and/or intrinsic ageing of the skin, or for slowing down the effects thereof, and/or as a cosmetic agent for depigmenting, bleaching or lightening the skin and keratin fibres (the hair, body hair), in a cosmetic composition.

Preferably, the water of the invention is used as a cosmetic agent
for stimulating the expression of the gene encoding HSP-70 and/or of the gene encoding involucrin, and/or
for inhibiting the genes encoding MMP-1 and/or MMP-3 and/or tyrosinase related protein-1 (TRP-1) and/or tyrosinase.

According to one embodiment, the invention relates to the use of a water as defined above,
as a cosmetic agent for depigmenting, bleaching or lightening the skin and keratin fibres, and/or
as a cosmetic agent for inhibiting the expression of the gene encoding Tyrosinase Related Protein-1 (TRP-1) and/or of the gene encoding tyrosinase,
in a cosmetic composition.

According to another embodiment, the invention relates to the use of a water as defined above, as a cosmetic agent for the protection and the prevention of extrinsic and/or intrinsic ageing of the skin, or for slowing down the effects thereof.

As explained, this water has an activity as an agent for the protection and the prevention of extrinsic and/or intrinsic ageing of the skin and/or as a melanogenesis-inhibiting agent.

Owing to this activity, it can be used as an active agent for preventing or delaying the appearance of the signs of intrinsic and/or extrinsic ageing of the skin, or for slowing down the effects thereof, and/or as a depigmenting, lightening or bleaching agent in cosmetic or dermatological compositions.

According to a second subject, the present invention relates to a cosmetic or dermatological composition comprising at least one water as defined above.

According to one preferred variant, the concentration by weight of the water of the invention relative to the total weight of the composition is at least 15%, preferably at least 40%, preferably at least 60%, and more preferably at least 80%.

The composition of the invention is advantageously a cosmetic or dermatological composition comprising, as active agent, at least one water as defined above, and at least one excipient, such as a cosmetically or dermatologically acceptable excipient.

According to one embodiment, the composition is a composition for preventing or delaying the appearance of the signs of intrinsic and/or extrinsic ageing of the skin, or for slowing down the effects thereof, and/or a composition for depigmenting, bleaching or lightening the skin and keratin fibres.

The composition according to the invention is advantageously intended for topical application.

The composition of the invention may advantageously a topical composition and may be formulated in the form of a solution, serum, lotion, spray, milk, emulsion, preferably of the oil-in-water type, or hydrogel.

According to one particular embodiment, the composition of the invention comprises at least one other active agent and at least one cosmetically or dermatologically acceptable excipient.

According to a first aspect, the composition aims to prevent or delay the appearance of the effects of intrinsic and/or extrinsic ageing of the skin, or to slow down the effects thereof.

It may also advantageously comprise one or more other active agents that can be chosen from substances having a free-radical-scavenging activity; substances intended to reduce or delay the effects of ageing of the skin, in particular the formation of wrinkles, by means of an activity aimed at promoting maintenance of the structure of the skin and/or at limiting degradation of the extracellular matrix of the superficial layers of the dermis and of the epidermis and/or at obtaining a skin protecting, correcting or restructuring effect; and substances having an anti-inflammatory activity.

According to a second aspect, the composition aims to depigment the skin and keratin fibres, in particular to lighten the complexion or to improve the uniformity of the skin coloration, or else to correct or reduce pigmentary skin spots or hyperpigmented skin areas.

It may also advantageously comprise one or more other active agents that can be chosen from substances having a depigmenting activity or a lightening activity on the skin and keratin fibres, or a bleaching activity on the skin and keratin fibres.

The depigmenting agents known to those skilled in the art are, for example, arbutin, kojic acid, azelaic acid, ferulic acid, vitamin B3 or PP, calcium D-pantetheine-S-sulphonate, resorcinol derivatives, resveratrol, extracts of liquorice or of white mulberry, alpha-lipoic acid, linoleic acid, cation-chelating agents such as EDTA (ethylenediaminetetraacetic acid), an extract of soya, an extract of Citrus unshiu, diacetyl boldine, retinol, a retinol ester such as retinyl propionate or retinyl palmitate, beta-ecdysone, tocopherol derivatives such as tocopheryl phosphate or potassium ascorbyl tocopheryl phosphate.

It may also comprise other active agents, having other cosmetic activities, that can be chosen, for example, from substances having a slimming activity; substances having a moisturising activity; substances having a calming, soothing or relaxing activity; substances having a skin microcirculation-stimulating activity for improving the radiance of the complexion, in particular of the face; substances having a sebum-regulating activity for greasy skin care; and substances intended for cleansing or purifying the skin.

The composition according to the invention also advantageously comprises at least one cosmetically or dermatologically acceptable excipient, that can be advantageously chosen from polymers, surfactants, rheological agents, fragrances, electrolytes, pH adjustors, antioxidants, preservatives, dyes, pearlescent agents and pigments, and mixtures thereof.

In a third subject, the invention relates to the use of the water of the invention as described above, in a cosmetic or dermatological composition or for the preparation of a cosmetic or dermatological composition, in which said composition is intended for:

preventing or delaying the appearance of the signs of intrinsic and/or extrinsic ageing of the skin, or slowing down the effects thereof;

preventing or reducing pigmentary spots on the skin (areas of hyperpigmentation) or the coloration of hyperpigmented areas of skin, in particular those consisting of various dyschromias of the skin, in particular contact dermatoses, drug-induced photodermatoses, melasma, keratoses, for example senile or actinic keratoses, senile lentigo (age spots) or solar lentigo, pigmentary spots resulting from scars or burns, or pigmentary spots induced by allergic or phototoxic reactions;

preventing or reducing the pigmentation of the periphery of depigmented areas, in particular induced by leucoderma such as vitiligo;

improving the uniformity of the skin coloration; or else lightening the complexion of the skin.

According to a fourth subject, the present invention relates to a nontherapeutic cosmetic care method or a dermatological treatment method comprising the topical application of at least one water or of a composition as defined above.

According to one particular embodiment, the cosmetic care method is intended for producing an aesthetic improvement in the appearance of the skin, without having a therapeutic effect, and in particular for:

preventing or delaying the appearance of the signs of intrinsic and/or extrinsic ageing of the skin, or slowing down the effects thereof;

preventing or reducing pigmentary spots on the skin (areas of hyperpigmentation) or the coloration of hyperpigmented areas of skin, in particular those consisting of various dyschromias of the skin, in particular contact dermatoses, drug-induced photodermatoses, melasma, keratoses, for example senile or actinic keratoses, senile lentigo (age spots) or solar lentigo, pigmentary spots resulting from scars or burns, or pigmentary spots induced by allergic or phototoxic reactions;

preventing or reducing the pigmentation of the periphery of depigmented areas, in particular induced by leucoderma such as vitiligo;

improving the uniformity of the skin coloration; or else lightening the complexion of the skin.

The present invention relates in particular to a cosmetic care method for the skin and keratin fibres, comprising the application, to at least one area of the skin exhibiting signs of extrinsic and/or intrinsic ageing of the skin and/or to at least one hyperpigmented area of bodily or facial skin or keratin fibres, of an effective amount of at least one cosmetic composition as defined above.

All the characteristics which have been described in relation to the first three subjects of the invention apply to the nontherapeutic cosmetic care method and also to the dermatological treatment method according to the invention.

For any aspect of the invention, the term "effective amount" is intended to mean an amount which is at least equal to the amount necessary for producing the specified cosmetic effect.

Other purposes, characteristics and advantages of the invention will become clearly apparent to those skilled in the art following reading of the explanatory description which makes reference to examples given by way of illustration and which could in no way limit the scope of the invention.

The examples form an integral part of the present invention and any characteristic derived from the description taken as a whole, including the examples, appearing to be novel over any prior art, forms an integral part of the invention in terms of its function and its generality.

Furthermore, in the examples, all percentages are given by weight, unless otherwise indicated, and the temperature is expressed in degrees Celsius unless otherwise indicated, and the pressure is atmospheric pressure, unless otherwise indicated.

Figure 1:
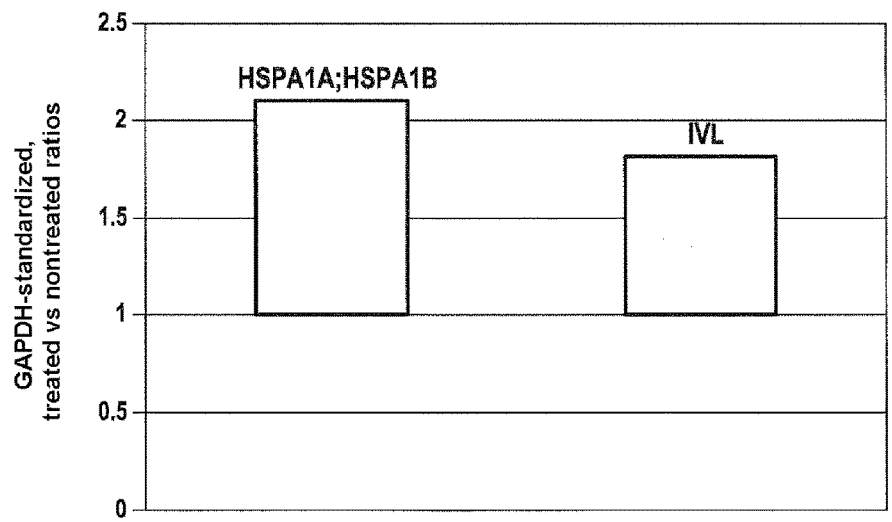
FIG. 1 relates to a histogram representing the effect of a water of the invention (EI), called "Iceland water" or "Icelandic Glacial® water", on the expression of the gene encoding HSP 70 (HSPA1A/HSPA1B) and of involucrin (IVL) of normal human keratinocytes (NHKs). This figure relates more particularly to the effect of the Iceland water on the level of transcripts of the genes encoding HSP-70 and involucrin in NHKs after 8 hours of treatment. The results presented in FIG. 1 are expressed according to a ratio of treated/nontreated (NT) standardized by means of the GAPDH reference gene.
Figure 2:
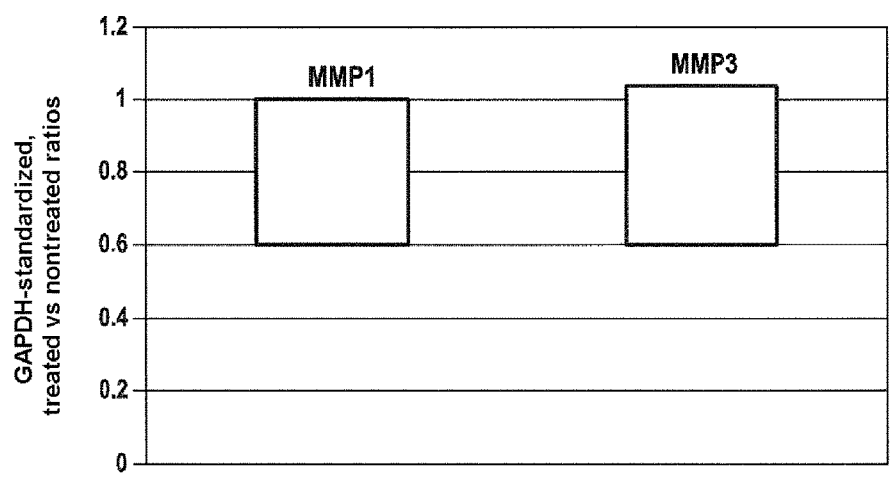
FIG. 2 relates to a histogram representing the effect of a water of the invention (EI) on the expression of the gene encoding MMP-1 and MMP-3 of normal human fibroblasts (NHFs). This FIG. 2 relates more particularly to the effect of the Iceland water on the level of transcripts of the MMP-1 and MMP-3 genes in NHFs after 24 hours of treatment.

The results presented in FIGS. 1 and 2 are expressed according to a ratio of treated/nontreated (NT) standardized by means of the expression of the GAPDH invariant reference gene.

Figure 3:
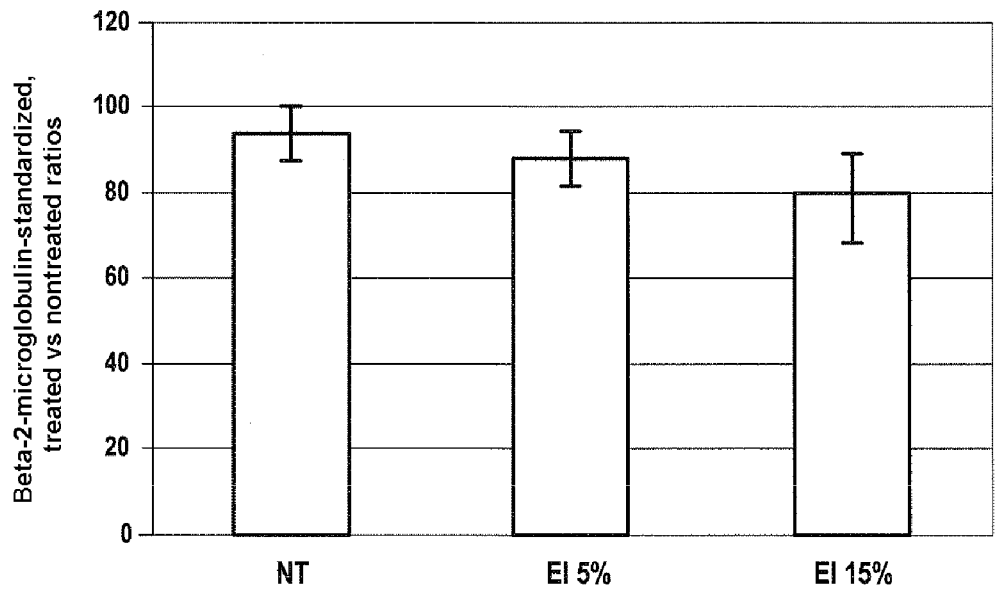

FIG. 3 relates to a histogram representing the effect of a water of the invention (EI) on the expression of the gene encoding the tyrosinase of normal human melanocytes. In particular, FIG. 3 relates to the effect of the Iceland water on the level of transcripts of the tyrosinase gene in normal human melanocytes treated for 24 hours.

Figure 4:
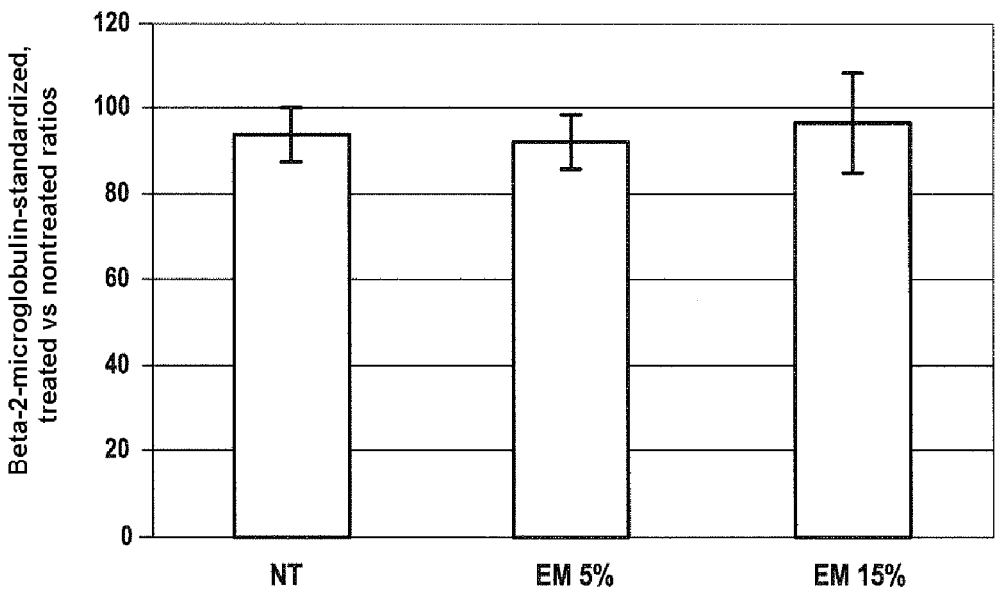

FIG. 4 relates to a histogram representing the effect of Milli-Q® water (EM) on the expression of the gene encoding the tyrosinase of normal human melanocytes. In particular, FIG. 4 relates to the effect of Milli-Q® water on the level of transcripts of the tyrosinase gene in normal human melanocytes treated for 24 hours.

Figure 5:
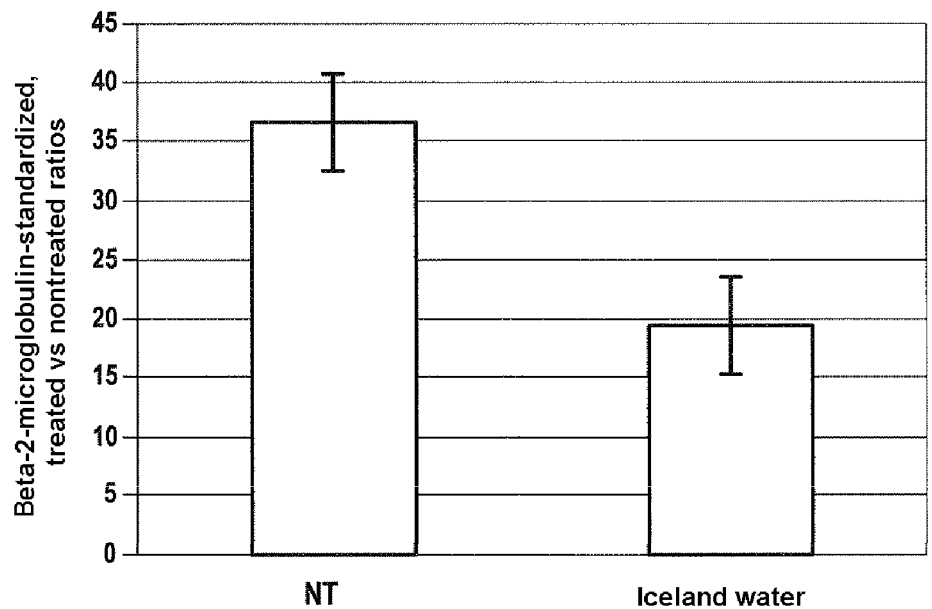

FIG. 5 relates to a histogram representing the effect of a water of the invention (EI) on the expression of the gene encoding the TRP-1 of normal human melanocytes. In particular, FIG. 6 relates to the effect of the Iceland water on the level of transcripts of the TRP-1 gene in normal human melanocytes treated for 24 hours.

Figure 6:
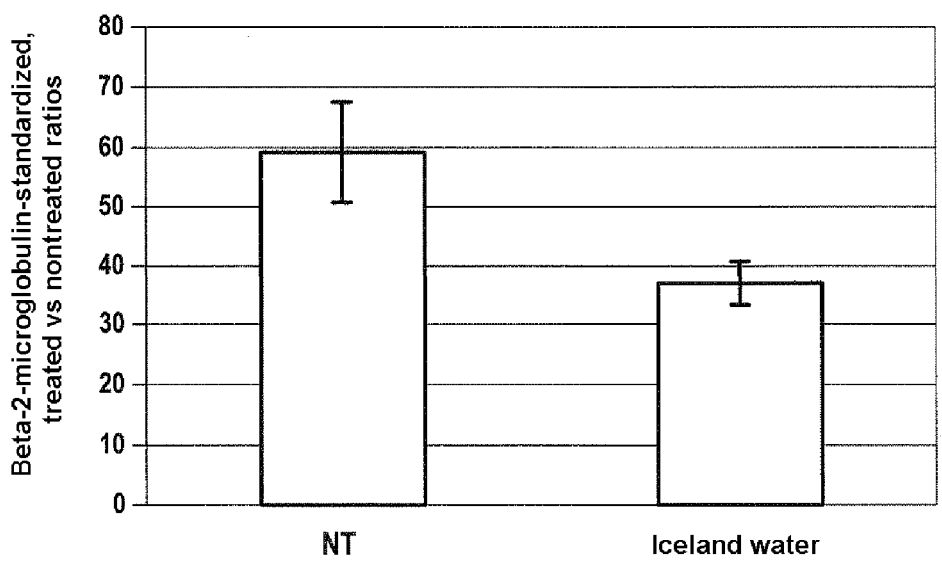

FIG. 6 relates to a histogram representing the effect of a water of the invention (EI) on the expression of the gene encoding the tyrosinase of normal human melanocytes. In particular, FIG. 6 relates to the effect of the Iceland water on the level of transcripts of the tyrosinase gene in normal human melanocytes treated for 24 hours.

Figure 7:
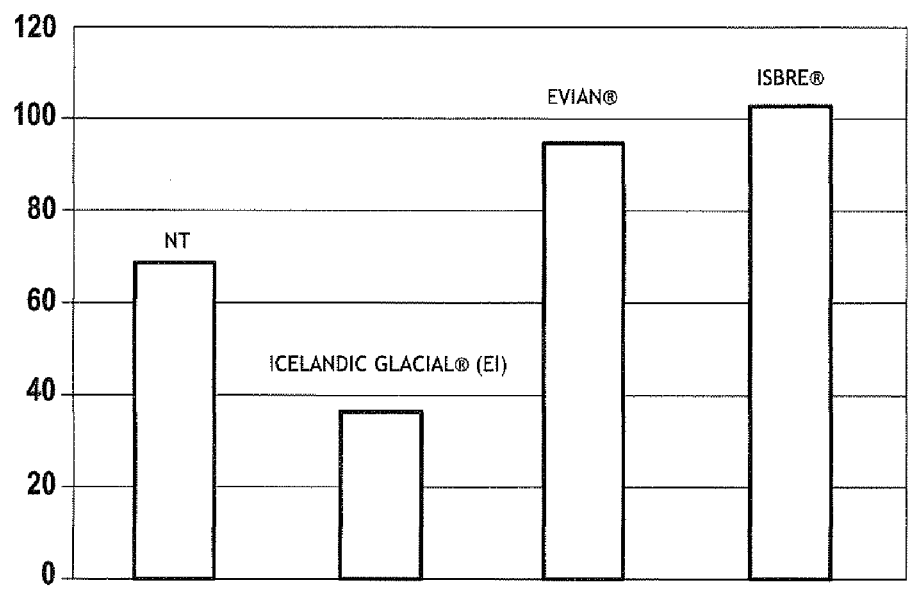

FIG. 7 relates to a histogram representing the effect of various waters, including a water of the invention, on the expression of the gene encoding the tyrosinase of normal human melanocytes treated for 24 hours.

The results presented in FIGS. 3 to 7 are expressed according to a ratio [treated/nontreated (NT)] standardized by means of the expression of the beta-2 microglobulin (β2-m) invariant reference gene.

In FIGS. 3 to 7, the Student's statistical test was used to compare the transcriptional effect between the treated cells and the nontreated cells (NT).

EXAMPLES

In the examples hereinafter, the term "water" used alone refers to a purified laboratory water. The water of the invention (EI) used in the examples is Icelandic Glacial® water, the water from a spring located in Iceland and sold under the name "Icelandic Glacial® water". This water is also called "Iceland Water" in the examples hereinbelow.

Example 1

Effect of Treatment with a Water of the Invention on the Expression of Genes Involved in Cell and Tissue Protection of the Epidermis The objective of this study was to evaluate the effect of a water of the invention on the expression of the genes encoding HSP-70 and involucrin.

1. Cell Culture

The normal human keratinocytes (NHKs) used were derived from a Caucasian adult donor. The NHKs were seeded into 6-well plates in a proportion of $2.5 \times 10^4$ cells/well in medium 1. Three wells of NHKs were seeded per culture condition, this being for a treatment of 8 hours.

2. Treatment

At 80% confluence, the cells were optionally treated with 15% of Iceland water in medium 1 below:

|  | Supplier |
|---|---|
| Epilife | Fisher |
| Supplements | Fisher |

After 8 hours of treatment, the cells were recovered in order to extract the total RNAs therefrom.

3. PCR Taqman Low Density Array 3.1 Obtaining of Total RNAs

The cell culture medium was removed, and 250 µl of RLT lysis buffer (supplied in the Nucleospin RNA trace kit) were added. The cells were scraped using a *Cell Scraper* and then the cell lysate was recovered in a 1.2 ml deepwell (supplied in the kit). The total RNAs were extracted using an Epimotion 5075 (Eppendorf) with the Nucleospin RNA trace kit (Macherey Nagel).

The total RNA solutions obtained were assayed and their quality was verified, using the Bioanalyseur 2100 (Agilent Technologies). This instrument was connected to a computer which had the specific result analysis software (2100 expert software). The technique required a 12-well microplate (RNA 6000 NanoChips) and a kit of reagents (RNA 6000 Nano Reagents & Supplies), specific for assaying eukaryotic total RNAs.

3.2 Synthesis of Complementary DNAs

The reverse transcription (RT) kit used was the High Capacity cDNA Reverse Transcription Kit (Applied Biosystems). 100 ng of total RNAs were diluted in water to give a final volume of 50 µl. They were then incubated for 10 minutes at 25° C. and then for 2 hours at 37° C. with 50 µl of 2× reaction mixture from the high capacity reverse transcription kit, prepared beforehand as indicated below.

| Reagents | volume |
|---|---|
| RT buffer | 10 µl |
| dNTP buffer | 4 µl |
| Random primer | 10 µl |
| RNAse out | 1 µl |
| RT | 5 µl |
| H$_2$O | 20 µl |

3.3 PCR Taqman Low Density Array

50 µl of each RT were sampled and mixed with 50 µl de "Taqman Gene Expression master mix". After homogenization, the 100 µl were deposited on the microfluidic cards, and the latter were centrifuged and then sealed.

Control genes were used to standardize the results. The PCR was carried out according to the protocol supplied by Applied Biosystems, in the ABI Prism 7900HT Sequence detection system apparatus. The steps of the qPCR were 2 min at 50° C., 10 min at 94.5° C. then 30 s at 97° C. and 1 min at 59.7° C., for 40 cycles.

4. Analysis of the Results

In the RT-PCR TLDA method, the quantification is carried out using the ΔCt comparative method. This method determines the number of cycles (Ct) of each gene of the card using the RQ Manager software which takes into account the background noise for each gene. This number of cycles (Ct) was standardized relative to the Ct of a GAPDH housekeeping gene invariant in the cells.

The results are presented in FIG. 1.

The increase (×2.1) in expression of the genes encoding HSP 70, observed after treatment with a water of the invention, Icelandic Glacial® water, conferred on the keratinocytes a better resistance to stresses and to external attacks. Consequently, the keratinocytes may secrete less cytokines and chemokines, which are pro-inflammatory factors involved in extracellular matrix degradation and the stimulation of melanogenesis. Likewise, the stimulation (×1.8) observed after treatment with a water of the invention, Icelandic Glacial® water, of the expression product of the gene encoding involucrin, which is a key factor in keratinocyte differentiation, allows the formation of an epidermal barrier which is protective with respect to external attacks.

Example 2

Effect of Treatment with a Water of the Invention on the Expression of Genes Involved in Cell and Tissue Protection of the Dermis The purpose of this study was to study the biological activity of Icelandic Glacial® water on a culture of normal human fibroblasts (NHFs) cultured in monolayer. As in Example 1, the study was carried out by means of the TLDA technology, TLDA standing for Taqman Low Density Array. The modulation of the expression of a panel of genes, encoding proteins specific for fibroblast-related biological pathways, in response to a treatment for a period of 24 h with Icelandic Glacial® water, was studied.

Metalloproteinases 1 and 3 (MMP-1 and MMP-3) belong to the same proteolytic cascade and act in concert in the degradation of collagens and more particularly collagens 1 and 3. They are particularly induced during ageing of the skin and in response to UV exposures. It is therefore strategic to want to inhibit expression, so as to control the degradation of the derman extracellular matrix.

1. Materials and Methods

Cell Culture

The normal human fibroblasts (NHFs) used were derived from a Caucasian adult donor.

The cells were seeded into 6-well plates in a proportion of $2.5 \times 10^4$ cells/well in medium 1 having the composition below:

Medium 1

|  | Supplier | Final concentration |
| --- | --- | --- |
| FCS | Biowest | 10% |
| DMEM | Fisher | qs |

Three wells of NHFs were seeded per culture condition. 24 hours before the treatment, at confluence, the cells were depleted of foetal calf serum (medium 2 having the composition below):

Medium 2

|  | Supplier |
| --- | --- |
| DMEM | Fisher |

2. Treatment

After 24 hours of culture without foetal calf serum, the cells were optionally treated with 15% of Icelandic Glacial® water in medium 2. After 8 and 24 hours of treatment, the cells were recovered in order to extract the total RNAs therefrom.

3. PCR Taqman Low Density Array

The method was in accordance with that of Example 1.

4. Results

After 24 hours of treatment, the NHFs were recovered in order to extract the total RNAs therefrom.

The results obtained demonstrate that the treatment of the NHFs with Icelandic Glacial® water at 15% by weight makes it possible to significantly decrease (respectively by 44% and 40%) the expression of MMP-1 and of MMP-3 after 24 hours of treatment (FIG. 2).

The effect of the Icelandic Glacial® water on the expression of these two metalloproteinases is particularly advantageous for preventing or slowing down ageing of the skin, by acting on ECM degradation.

Example 3

Effect of Treatment with Waters of Different Composition, Including a Water of the Invention, on the Expression of Genes Involved in Melanogenesis and Skin Pigmentation Defects The objective of this study was to evaluate, on normal human melanocytes (NHMs), by real-time quantitative RT-PCR (qRT-PCR), the effect of an active agent, Icelandic Glacial® water, on the expression of the genes encoding tyrosinase-related protein 1 (TRP-1) or tyrosinase.

The effect of this active agent was optionally compared, in the tests below, with waters not in accordance with the invention.

Cell Culture

Normal human melanocytes (NHMs) from a donor 1 were placed in culture and seeded into 6-well plates in a proportion of $2.5 \times 10^5$ cells/well in medium 3 (composition below). Three wells were seeded per culture condition; three non-treated control wells and three wells treated for a treatment time of 24 hours.

Composition of Medium 1:

|  | Supplier | Final concentration |
| --- | --- | --- |
| Medium E-199 with glutamax | Fisher |  |
| Foetal calf serum | Abcys | 10% |

Composition of Medium 2:

|  | Supplier | Final concentration |
| --- | --- | --- |
| KSFM | Fisher |  |
| Pituitary extracts | Fisher | 50 µg/ml of KSFM |

Composition of Medium 3:

|  | Supplier | Final concentration |
| --- | --- | --- |
| Medium 2 |  | 90% |
| Medium 1 |  | 10% |
| b-Fibroblast Growth Factor | Fisher | 10 ng/ml |

Treatment of Melanocytes 48 hours after the seeding, the cells were treated by bringing into contact with a water of the invention or a water having a composition different from Icelandic Glacial® water (treatment conditions specified in paragraphs 1.1 to 1.3), diluted in medium 3, filtered through a 0.22 µm filter. A nontreated control was also prepared.

After 24 hours of treatment, the cells were recovered in order to extract the total RNAs therefrom.

Obtaining of Total RNAs Using the Rneasy Kit (Qiagen)

The cell culture medium was removed, and 350 μl of RLT lysis buffer (supplied in the kit) were added. The cells were scraped using a cell scraper and the cell lysate was homogenized using a syringe.

The total RNAs were extracted according to the supplier's protocol.

The total RNA solutions thus obtained were assayed. The technique required a 12-well microplate (RNA 6000 Nano-Chips) and a kit of reagents (RNA 6000 Nano Reagents & Supplies) specific for the assaying of eukaryotic total RNAs.

Synthesis of Complementary DNAs

The reverse transcription (RT) kit used is the "High Capacity cDNA Reverse Transcription Kit, 1000 Reactions" (Applied Biosystems), used according to the supplier's protocol. 100 ng of total RNAs, after DNAse, were diluted in water to give a final volume of 25 μl. They were then incubated for 10 minutes at 25° C. and then for 2 hours at 37° C. with 25 μl of 2× reaction mixture from the High capacity cDNA archive kit, prepared beforehand as indicated below.

| Reagents | Volume |
|---|---|
| RT buffer | 10 μl |
| dNTP buffer | 4 μl |
| Random primer | 10 μl |
| RNAse out | 1 μl |
| RT | 5 μl |
| H$_2$O | 20 μl |

Real-Time Quantitative RT-PCR

Reagents used for the analysis

| | Supplier |
|---|---|
| Kit RNeasy | Qiagen |
| RNAse out | Invitrogen |
| Taqman Fast Universal master mix | Applied |
| TaqMan β2-m expression | Applied |
| Taqman TRP-1 expression | Applied |
| Taqman Tyrosinase expression | Applied |

The effect of the treatments was evaluated by real-time quantitative PCR (qRT-PCR) with the 7900HT fast 96-well block from Applied Biosystems.

Preparation of the Reaction Mixture for 1 Reaction:

| TaqMan Fast universal PCR master mix (2x) | 10 μl |
|---|---|
| TaqMan gene expression assay | 1 μl |
| H$_2$O | 4 μl |

The 15 μl of the mixture were placed in the wells of a 96-well plate specially designed for the 7900HT instrument, and 5 μl of water (for the blank) or 5 μl of successive dilutions of cDNA (for the range) or 5 μl of samples diluted to 1/50 in purified water, irrespective of the gene, were added to the corresponding wells.

Analysis of the Results

For each sample, the number of cycles at which the signal appears was determined using the SDS 2.3 software (Applied Biosystems), and by virtue of the calibration line established with the calibration range, the concentration in terms of number of copies of transcript could thus be calculated.

For the same assay, the expression levels of the TRP-1 and tyrosinase transcripts obtained were standardized relative to the value obtained for the β2-m gene. This gene, the expression of which is constitutive and invariant, made it possible to be free of any variation in amounts between assays, and in particular those due to different reverse transcription efficiencies.

Statistical Analysis

Statistically significant transcriptional activity variations were evaluated by applying the Student's test.

Each condition was carried out in triplicate (3 nontreated controls and 3 treated). The Fischer test was first of all applied by comparing the two data matrices. When the Fischer test was greater than 0.05, then the variance for the Student's test was equal to 2. When the Fischer test was less than 0.05, then the variance was equal to 3.

The transcriptional variations retained were those which had a Student's test of less than 0.05. The data presented in the results section are the ratios of the amounts obtained in the treated samples versus the nontreated control samples, the whole related back to the invariant β2-microglobulin (β2-m) gene.

Results 1.1—Effect of Treatment with a Concentration Range of Iceland Water (Water of the Invention) on the Expression of the Tyrosinase Gene in NHMs after 24 Hours of Treatment The effect of the Iceland water (water of the invention) was compared with that produced by a highly purified and deionized water sold under the name Milli-Q® (supplier Millipore).

Normal human melanocytes, from a donor 1, seeded into 6-well plates were treated, at confluence, in triplicate, with 5 or 15% of Iceland water or of Milli-Q® water for 24 hours. A nontreated control was also prepared.

The level of transcripts encoding the gene encoding tyrosinase was measured for a sample and related back to the level of transcripts encoding the invariant β2-m gene.

The results obtained were processed in the form of histograms.

FIG. 3 shows a decrease in the level of transcripts of the gene encoding tyrosinase of 16% after 24 hours of treatment with the Iceland water.

FIG. 4 shows that the Milli-Q® water has no effect on tyrosinase gene expression.

Unlike the Milli-Q® water, a water of the invention makes it possible to significantly inhibit the expression of the gene encoding tyrosinase, which is a key enzyme in melanogenesis and in skin pigmentation.

1.2—Effect of Treatment with a Water of the Invention on the Expression of the Gene Encoding TRP-1 in NHMs after 24 Hours of Treatment Normal human melanocytes, derived from a donor 2, seeded into 6-well plates, were treated, at confluence, in triplicate, with 15% of Iceland water for 24 hours. A nontreated control was also prepared. The level of transcripts encoding the TRP-1 gene was measured for a sample and related back to the level of transcripts encoding the invariant β2-m gene.

The results obtained are processed in the form of histograms.

FIG. 5 shows a decrease in the level of transcripts of the TRP-1 gene of 47.10% after 24 hours of treatment with the Iceland water.

A water of the invention makes it possible to significantly inhibit the expression of the gene encoding TRP-1 involved in melanogenesis and in skin pigmentation.

1.3—Effect of Treatment in Normal Human Melanocytes with a Water of the Invention at 15% on the Expression of the Gene Encoding Tyrosinase after 24 Hours of Treatment Normal human melanocytes derived from a donor 2, seeded into 6-well plates, were treated at confluence, in triplicate, with 15% of Iceland water for 24 hours. A nontreated control was also prepared.

The level of transcripts encoding the tyrosinase gene was measured for a sample and related back to the levels of transcripts encoding the invariant $\beta$2-m gene.

The results obtained were processed in the form of histograms.

FIG. 6 shows a decrease in the level of transcripts of the gene encoding tyrosinase of 37.60% after 24 hours of treatment with the Iceland water.

1.4—Compared Effects of Treatment with a Water of the Invention and a Mineral Water on the Expression of the Tyrosinase Gene in NHMs after 24 Hours of Treatment The effect produced by the Iceland water (water of the invention) was compared with that produced by a mineral water sold under the name "Evian® water", and a very pure glacier water, the characteristics of which (composition, pH, TDS) are different from those of the water of the invention. Table 3 below gives the respective characteristics of the Icelandic Glacial® water (water of the invention) and of the Evian® water which is not in accordance with the invention (data obtained on the websites of the manufacturers, addresses below).

TABLE 3

| (Concentrations expressed in mg/ml) | Icelandic Glacial ® www.icelandicglacial.com | ISBRE ® www.isbre.com | EVIAN ® www.evian.com |
|---|---|---|---|
| Calcium ($Ca^{2+}$) | 6.4 | 0.8 | 80 |
| Chlorine ($Cl^-$) | 13 | 1.2 | 6.8 |
| Magnesium ($Mg^{2+}$) | 2.4 | 0.1 | 26 |
| Potassium ($K^+$) | 0.6 | 0.8 | 1 |
| Sodium ($Na^+$) | 12 | 0.5 | 6.5 |
| Bicarbonates ($HCO_3^-$) | 33 | 0 | 360 |
| Sulphates ($SO_4^{2-}$) | 3.4 | 1.3 | 12.6 |
| TDS | 62 | 4 | 357 |
| pH | 8.4 | 5.7 | 7.2 |

It is in particular noted that the Iceland water is more alkaline than the other two waters tested. It has a lower mineral load than the Evian® water (cf. calcium or bicarbonates). However, it contains more minerals than the Isbre® glacier water, reputed to be very pure, the TDS value of which is 4.

Normal human melanocytes were treated, at confluence, in triplicate, with 15% of Iceland water or of Evian® water for 24 hours. A nontreated control was also prepared.

The level of transcripts encoding the gene encoding tyrosinase was measured for a sample and related back to the levels of transcripts encoding the invariant $\beta$2-m gene.

The results obtained were processed in the form of histograms.

FIG. 7 shows a decrease in the level of transcripts of the gene encoding tyrosinase of 16% after 24 hours of treatment with the Iceland water.

The Icelandic Glacial® water, which is a water of the invention, makes it possible to significantly inhibit the expression of the gene encoding tyrosinase, and thus to act on melanogenesis and skin pigmentation.

On the other hand, a more mineralized water (Evian®) or conversely a very weakly mineralized water (Isbre®) or a totally demineralized water) (Milli-Q®), shows no effect on the expression of the gene encoding tyrosinase.

CONCLUSION

This study made it possible to show that a water of the invention partially inhibits the transcription of the genes encoding tyrosinase and encoding tyrosinase-related protein 1 (TRP-1) in normal human melanocytes (NHMs). The treatment for 24 hours with the Iceland water leads to a significant decrease in the expression of the genes encoding TRP-1 and tyrosinase, contrary to the effects noted for waters of which the characteristics are not in accordance with those of the invention.

Thus, a water of the invention, particularly the Icelandic Glacial® water, can be used as a skin-depigmenting, -bleaching or -lightening active agent, in a cosmetic composition.

Example 4

Cosmetic Formulations According to the Invention

Compositions were prepared according to the formulae below, in which the percentages are expressed by weight relative to the final composition, and the name of the ingredients corresponds to their chemical name, their brand name or their INCI name.

4.1—Anti-Ageing Serum

An anti-ageing serum was prepared according to the formula below.

|  | % by weight |
|---|---|
| Glycerol | 5 |
| Butylene glycol | 3 |
| Pentylene glycol | 3 |
| Polyglycerol-3 | 2.5 |
| Methyl gluceth-20 | 1.8 |
| Decyloxazolidone | 1 |
| Phenoxyethanol | 9 |
| Talc | 1 |
| Lecithin | 1 |
| Carbomer | 0.5 |
| Sorbitol | 3 |
| Silica | 0.2 |
| Alumina | 0.2 |
| Sodium hydroxide | 0.2 |
| Algin | 0.1 |
| Polyvinyl alcohol | <0.1 |
| Sodium hyaluronate | <0.1 |
| Mallow (*Malva sylvestris*) extract | 0.7 |
| Hydrolysed soya flour | <0.1 |
| Adenosine | <0.1 |

| | % by weight |
|---|---|
| Ascorbic acid | <0.1 |
| Extract of *Hibiscus esculentus* fruit | <0.1 |
| Icelandic Glacial ® water | 77 |

The lotion is a fluid aqueous composition comprising the water of the invention, which is applied to the face in the morning and evening. Its composition comprising the water of the invention allows a preventive effect with respect to the signs of appearance of ageing of the skin, in particular a loss of radiance of the complexion or of firmness of the skin.

4.2—Light Anti-Ageing Cream

| | % by weight |
|---|---|
| Caprylic/capric triglyceride | 10 |
| Glycerol | 5 |
| Cetearyl alcohol | 4 |
| Butylene glycol | 3 |
| Pentylene glycol | 3 |
| Mango (*Mangifera indica*) butter | 1.5 |
| Glyceryl stearate | 1.2 |
| Decyloxazolidone | 1 |
| Steareth-21 | 1 |
| Phenoxyethanol | 0.9 |
| Cetearyl glucoside | 0.8 |
| Hydrogenated cocoglycerides | 0.7 |
| Talc | 0.6 |
| Sorbitol | 0.5 |
| Dimethicone | 0.5 |
| Cetyl palmitate | 0.3 |
| Algin | 0.2 |
| Cocoglycerides | 0.2 |
| Silica | 0.2 |
| Carbomer | 0.2 |
| Alumina | 0.2 |
| Xanthan gum | 0.1 |
| Polyvinyl alcohol | 0.1 |
| Titanium dioxide | 0.1 |
| Tromethamine | 0.1 |
| Cellulose gum | <0.1 |
| Sodium hyaluronate | <0.1 |
| Mallow (*Malva sylvestris*) extract | 0.7 |
| Hydrolysed soya flour | <0.1 |
| Adenosine | <0.1 |
| Ascorbic acid | <0.1 |
| Extract of *Hibiscus esculentus* fruit | <0.1 |
| Iceland Spring ® water | 73 |

The cream, the continuous aqueous phase of which consists of the water of the invention, was applied to the face and the neckline in the morning, with emphasis particularly on the areas showing signs of ageing of the skin. It makes it possible to obtain a protective effect with respect to extrinsic and/or intrinsic ageing of the skin.

4.3—Rich Anti-Ageing Cream

An oil-in-water emulsion was prepared according to the following composition:

| | % by weight |
|---|---|
| Caprylic/capric triglyceride | 15 |
| Glycerol | 5 |
| Cetearyl alcohol | 4 |
| Butylene glycol | 3 |
| Pentylene glycol | 3 |
| Mango (*Mangifera indica*) butter | 2 |
| Glyceryl stearate | 2.2 |
| Hydrogenated cocoglycerides | 2 |
| Dimethicone | 1 |
| Cetyl palmitate | 0.6 |

| | % by weight |
|---|---|
| Decyloxazolidone | 1 |
| Steareth-21 | 1 |
| Phenoxyethanol | 0.9 |
| Cetearyl glucoside | 0.8 |
| Talc | 0.6 |
| Sorbitol | 0.5 |
| Cocoglycerides | 0.5 |
| Silica | 0.2 |
| Algin | 0.3 |
| Carbomer | 0.2 |
| Xanthan gum | 0.1 |
| Polyvinyl alcohol | 0.1 |
| Tromethamine | 0.1 |
| Cellulose gum | <0.1 |
| Sodium hyaluronate | <0.1 |
| Mallow (*Malva sylvestris*) extract | 0.7 |
| Hydrolysed soya flour | <0.1 |
| Adenosine | <0.1 |
| Ascorbic acid | <0.1 |
| Extract of *Hibiscus esculentus* fruit | <0.1 |
| Ducale ® water | 55 |

The rich cream, the aqueous phase of which comprises the water of the invention, was applied to the face in the evening. It makes it possible to obtain a preventive effect with respect to extrinsic and/or intrinsic ageing of the skin.

4.4—Depigmenting Facial Day Gel Emulsion

A gel emulsion was prepared according to the composition below.

| | % by weight |
|---|---|
| Glycerol | 5 |
| Caprylic/capric/succinic triglycerides | 5 |
| Octyl methoxycinnamate | 1 |
| Dimethicone copolyol | 0.5 |
| Acrylates/$C_{10-30}$ alkyl acrylate crosspolymer | 0.5 |
| Ascorbyl-2 glucoside | 2 |
| Icelandic Glacial ® water | 90 |
| Preservatives, fragrance, dyes | qs. |

Some individuals subjected to more or less intense radiation from daylight, or even from the sun directly, wish to preserve a light complexion and to avoid the appearance of pigmented spots.

The use of the above gel emulsion makes it possible to achieve this objective. This composition is applied to the face generally in the morning. It acts preventively or curatively on the pigmentation, which may or may not be even, of the face.

4.5—Pigmentary Spot-Preventing SPF 30 Protective Fluid

A protective fluid was prepared according to the composition below:

| | % by weight |
|---|---|
| Volatile pentacyclomethicone | 49 |
| Titanium dioxide | 15 |
| Octyl methoxycinnamate | 7.5 |
| Glycerol | 5 |
| Phenyl trimethicone | 5 |
| Dimethicone copolyol | 3 |
| Poly(methyl methacrylate) | 2.5 |
| Butylmethoxydibenzoylmethane | 1 |
| Icelandic Glacial ® water | 15 |
| Neutralizer, fragrances, preservatives, antioxidants | qs. |

The protective fluid is used for preventing the appearance of pigmentary spots, in individuals predisposed to this phenomenon, before exposure to an intense solar radiation. It should be noted that the presence of a high concentration of sunscreen makes it possible to compensate for the decrease in natural protection resulting from the reduction in the level of melanin.

4.6—Depigmenting Face Cream

A cream was prepared according to the composition below:

|  | % by weight |
|---|---|
| Glyceryl stearate + Peg-100 stearate | 5 |
| Hydrogenated polyisobutene | 4 |
| Magnesium ascorbyl phosphate | 3 |
| Glyceryl tricaprylate/caprate | 3 |
| Squalane | 3 |
| Glycerol | 2 |
| Beeswax | 1 |
| Cetearyl octanoate | 1.5 |
| Cetyl alcohol | 1 |
| Stearyl alcohol | 1 |
| Dimethicone | 1 |
| Xanthan gum | 0.3 |
| Ethylenediaminetetraacetic acid | 0.2 |
| Potassium diglycerrhizinate | 0.2 |
| Tocopheryl acetate | 0.2 |
| Salicylic acid | 1 |
| Sodium citrate | 0.1 |
| Iceland Spring ® water | 70 |
| Neutralizer, fragrance, preservatives | qs. |

The use of this cream, which is in the form of an oil-in-water emulsion, makes it possible to treat the irregularities of the skin pigmentation, by reducing or eliminating senescence spots or actinic pigmentary spots. It makes the skin coloration uniform and lightens the complexion.

4.7—Face Lotion for Lightening the Complexion

A lotion was prepared according to the composition below:

|  | % by weight |
|---|---|
| Ethyl alcohol | 30 |
| PPG-3 myristyl ether | 5 |
| Glycerol | 2 |
| Carbomer | 0.2 |
| Butylene glycol | 3 |
| Polysorbate 20 | 0.2 |
| Calcium D-pantetheine-S-sulphonate | 0.2 |
| Extract of *Citrus unshiu* | 2 |
| Ducale ® water | 56 |
| Neutralizer, fragrance, preservatives | qs. |

This lotion for lightening the complexion is used after makeup removal and cleansing of the skin.

4.8—Lightening Face Serum

A serum was prepared according to the composition below:

|  | % by weight |
|---|---|
| Icelandic Glacial ® water | 88 |
| Glycerol | 2 |
| Tetrasodium EDTA/citric acid/trisodium citrate | qs desired pH |
| Xanthan gum | 0.25 |
| Burnet extract | 0.5 |
| Ascorbyl-2 glucoside | 2 |
| Polymethylsilsesquioxane | 2 |

-continued

|  | % by weight |
|---|---|
| Ethyl alcohol | 2 |
| Lactic acid | 1 |
| Polyacrylamide, $C_{13-14}$ isoparaffin, laureth-7 | 0.5 |
| Dimethicone copolyol | 0.25 |
| Fragrance, dye, preservative | qs |

A drop of this highly concentrated serum composition is applied to the face generally before application of a face cream. This serum is customarily used as treatments of one to two weeks in order to obtain or maintain a lightening of the complexion.

4.9—Hair Lotion for Lightening the Head of Hair

A hair lotion was prepared according to the composition below:

|  | % by weight |
|---|---|
| Iceland Spring ® water | 46 |
| Alcohol | 50 |
| Panthenyl ethyl ether | 0.5 |
| DL-alpha-tocopheryl acetate | 0.2 |
| Polysorbate 60 | 1 |
| Liquorice extract | 0.1 |
| Fragrance | 0.2 |
| Glycerol | 0.5 |
| Dye | qs |

This lotion is applied to the hair in the morning and the evening for several weeks, in order to obtain gradual lightening of the head of hair.

4.10—Anti-Spot Cream Gel for the Hands

A cream gel was prepared according to the composition below:

|  | % by weight |
|---|---|
| Ducale ® water | 69 |
| Caprylic/capric diglyceryl succinate | 6 |
| Octyl octanoate | 2.5 |
| Octyl methoxycinnamate | 6 |
| Ascorbyl-2-glucoside | 2 |
| Phenyl trimethicone | 2.5 |
| Benzophenone-3 | 0.5 |
| Sodium hyaluronate | 0.05 |
| Xanthan gum | 0 |
| Acrylates/C10-30 alkyl acrylate copolymer | 0.5 |
| Poly(methyl methacrylate) | 1 |
| Glycerol | 2 |
| PEG 150 | 3 |
| Neutralizers, dyes, fragrance, preservatives | qs |

This cream gel should be applied directly to the senescence spots (senile lentigines) on the hands, in order to reduce the coloration thereof.

In the examples, "qs" means "quantity sufficient", i.e. the quantity sufficient to take the total to 100%.

The invention claimed is:

1. A skin care method, comprising applying to keratin materials in which a disorder relating to an overproduction of melanin occurs, selected from the group consisting of pigmentary spots, hyperpigmented areas of skin, and the periphery of depigmented areas, of a subject in need thereof so as to reduce pigmentation of the pigmentary spots, hyperpigmented areas and periphery of depigmented areas, a cosmetic composition containing an effective amount of one pigmentation-reducing active agent, wherein the composition is applied to a keratin material having a disorder selected from the group consisting of contact dermatoses, drug-induced photodermatoses, melasma, keratoses, senile lentigo or solar lentigo, pigmentary spots resulting from scars or burns, pigmentary spots induced by allergic or phototoxic reactions, and leucoderma, wherein the active agent inhibits in melanocytes the expression of at least one selected from the group consisting of the gene encoding Tyrosinase Related Protein-1 (TRP-1) and the gene encoding tyrosinase, and wherein the active agent consists of a water having:
a pH of between 7.6 and 10, and
a total dissolved solids (TDS) concentration of between 10 and 250 mg/l, and comprising the following concentrations:
calcium ($Ca^{2+}$) between 3 and 14 mg/l;
chloride ($Cl^-$) between 2 and 16 mg/l;
magnesium ($Mg^{2+}$) between 0.8 and 5 mg/l;
potassium ($K^+$) between 0.01 and 2 mg/l;
sodium ($Na^+$) between 2 and 14 mg/l;
bicarbonates ($HCO_3^-$) between 0 and 50 mg/l;
sulphates ($SO_4^{2-}$) between 1 and 5 mg/l.

2. The method according to claim 1, wherein the water has a pH of between 7.8 and 8.8.

3. The method according to claim 1, wherein the water has a total dissolved solids (TDS) concentration of between 20 and 100 mg/l.

4. The method according to claim 1, wherein the composition is a dermatological composition further comprising an excipient.

5. The method according to claim 1, wherein the concentration by weight of water relative to the total weight of the composition is from 10% to 99%.

6. The method according to claim 1, wherein the composition is a topical composition further comprising a topical excipient.

7. The method according to claim 1, wherein the composition further comprises at least one other active agent that is not an active agent that can depigment or bleach the keratin materials.

8. The method according to claim 1, wherein the water has the following composition:
calcium ($Ca^{2+}$) approximately 6.4 mg/l;
chlorine ($Cl^-$) approximately 13 mg/l;
magnesium ($Mg^{2+}$) approximately 2.4 mg/l;
potassium ($K^+$) approximately 0.6 mg/l;
sodium ($Na^+$) approximately 12 mg/l;
bicarbonates ($HCO_3^-$) approximately 33 mg/l;
sulphates ($SO_4^{2-}$) approximately 3.4 mg/l;
wherein the water has a total dissolved solids (TDS) concentration of approximately 62 mg/l; and
wherein the water has a pH of approximately 8.4.

9. The method according to claim 1, wherein the water has the following composition:
calcium ($Ca^{2+}$) approximately 4.6 mg/l;
chlorine ($Cl^-$) approximately 11.0 mg/l;
magnesium ($Mg^{2+}$) approximately 0.9 mg/l;
potassium ($K^+$) approximately 0.5 mg/l;
sodium ($Na^+$) approximately 12 mg/l;
sulphates ($SO_4^{2-}$) approximately 2.3 mg/l;
wherein the water has a total dissolved solids (TDS) concentration of approximately 48 mg/l; and
wherein the water has a pH of approximately 8.7.

10. The method according to claim 1, wherein the water has the following composition:
calcium ($Ca^{2+}$) approximately 12.5 mg/l;
chlorine ($Cl^-$) approximately 3.8 mg/l;
magnesium ($Mg^{2+}$) approximately 1.3 mg/l;
potassium ($K^+$) approximately 0.4 mg/l;
sodium ($Na^+$) approximately 3 mg/l;
sulphates ($SO_4^{2-}$) approximately 6.9 mg/l;
wherein the water has a total dissolved solids (TDS) concentration of approximately 56 mg/l; and
wherein the water has a pH of approximately 8.3.

11. The method according to claim 1, wherein the concentration by weight of water relative to the total weight of the composition is at least 15%.

12. The method according to claim 1, wherein the composition is formulated in the form of a solution, serum, lotion, spray, milk, emulsion.

13. The method according to claim 1, wherein the water has a pH of between 8.2 and 8.8.

14. The method according to claim 1, wherein the water has a total dissolved solids (TDS) concentration of between 40 and 80 mg/l.

15. The method according to claim 1, wherein the composition is applied to a keratin material having senile keratosis or actinic keratosis.

16. The method according to claim 1, wherein the composition is applied to a keratin material having vitiligo.

17. The method according to claim 1, wherein the water comprises the following concentrations:
calcium ($Ca^{2+}$) between 4 and 10 mg/l;
chloride ($Cl^-$) between 8 and 14 mg/l;
magnesium ($Mg^{2+}$) between 0.8 and 3 mg/l;
potassium ($K^+$) between 0.1 and 1 mg/l;
sodium ($Na^+$) between 8 and 13 mg/l;
bicarbonates ($HCO_3^-$) between 10 and 40 mg/l;
sulphates ($SO_4^{2-}$) between 2 and 5 mg/l.

18. The method according to claim 11, wherein the concentration by weight of water relative to the total weight of the composition is at least 40%.

19. The method according to claim 11, wherein the concentration by weight of water relative to the total weight of the composition is at least 60%.

20. The method according to claim 11, wherein the concentration by weight of water relative to the total weight of the composition is at least 80%.

21. The method according to claim 12, wherein the composition is in the form of an oil-in-water emulsion or hydrogel.

* * * * *